(12) United States Patent
Suzuki

(10) Patent No.: US 11,331,046 B2
(45) Date of Patent: May 17, 2022

(54) PULSE OXIMETER

(71) Applicant: Nihon Kohden Corporation, Tokyo (JP)

(72) Inventor: Tetsuo Suzuki, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 930 days.

(21) Appl. No.: 16/110,074

(22) Filed: Aug. 23, 2018

(65) Prior Publication Data

US 2019/0059823 A1 Feb. 28, 2019

(30) Foreign Application Priority Data

Aug. 29, 2017 (JP) .............................. JP2017-164265

(51) Int. Cl.
*A61B 5/1455* (2006.01)
*A61B 5/00* (2006.01)

(52) U.S. Cl.
CPC ........ *A61B 5/7239* (2013.01); *A61B 5/14551* (2013.01); *A61B 5/7275* (2013.01)

(58) Field of Classification Search
None
See application file for complete search history.

(56) References Cited

U.S. PATENT DOCUMENTS

| 2004/0267140 | A1 | 12/2004 | Ito et al. |
| 2005/0197579 | A1 | 9/2005 | Baker, Jr. |
| 2007/0016085 | A1* | 1/2007 | Inukai ................ A61B 5/02125 600/485 |
| 2008/0146901 | A1 | 6/2008 | Katura et al. |
| 2015/0150513 | A1 | 6/2015 | Kobayashi et al. |

FOREIGN PATENT DOCUMENTS

| CN | 104706362 A | 6/2015 |
| JP | 2003-220052 A | 8/2003 |
| JP | 2005-095581 A | 4/2005 |
| JP | 2007-007075 A | 1/2007 |
| JP | 2007-527773 A | 10/2007 |
| JP | 4196209 B2 | 12/2008 |

OTHER PUBLICATIONS

Communication dated Nov. 17, 2020, from the Japanese Patent Office in counterpart application No. 2017-164265.

\* cited by examiner

*Primary Examiner* — Marjan Fardanesh
(74) *Attorney, Agent, or Firm* — Sughrue Mion, PLLC

(57) ABSTRACT

A pulse oximeter includes one or more processor and one or more memory storing instructions. When the instructions are executed by the one or more processor, the one or more processor causes the pulse oximeter to acquire a first signal corresponding to an intensity of first light having a first wavelength and a second signal corresponding to an intensity of second light having a second wavelength, set a presumptive value of an arterial oxygen saturation, acquire an arterial blood component signal and a venous blood component signal corresponding to the presumptive value from the first signal and the second signal, acquire an index value corresponding to a phase difference between the arterial blood component signal and the venous blood component signal, and calculate the arterial oxygen saturation based on a variation of the index value associated with a change of the presumptive value.

8 Claims, 8 Drawing Sheets

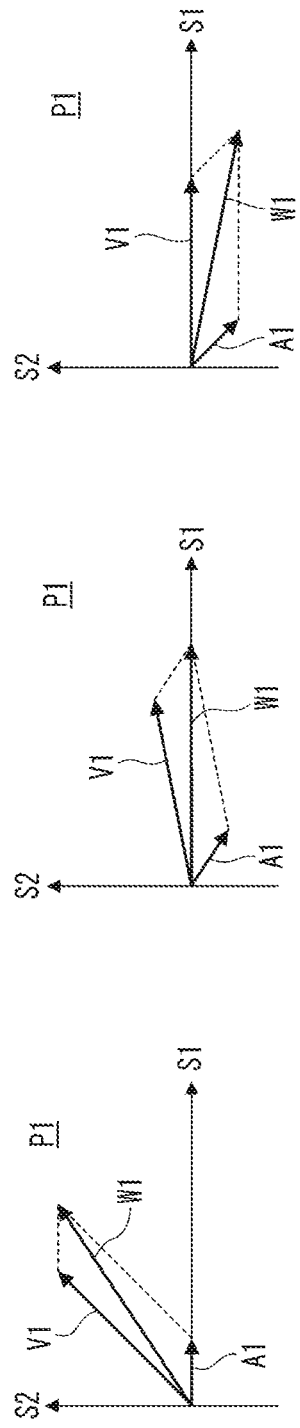
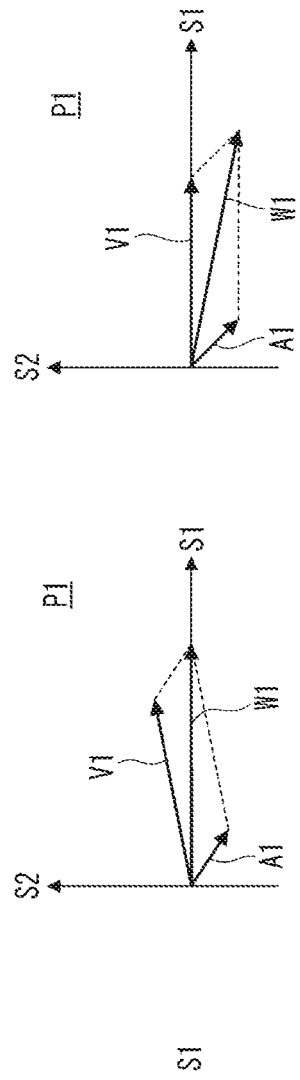
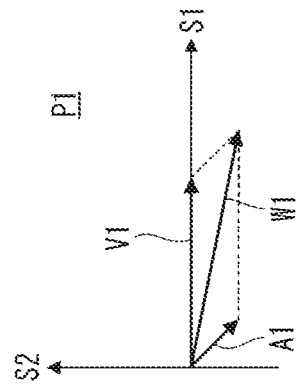
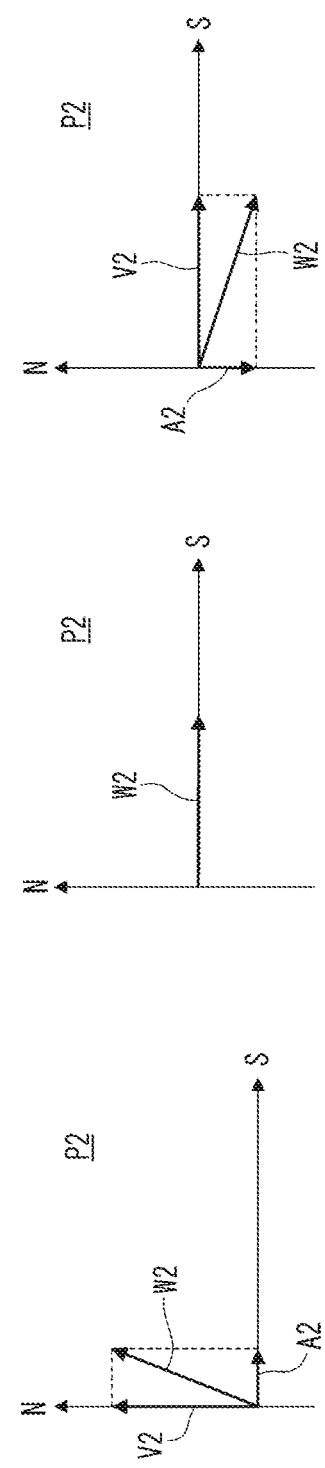
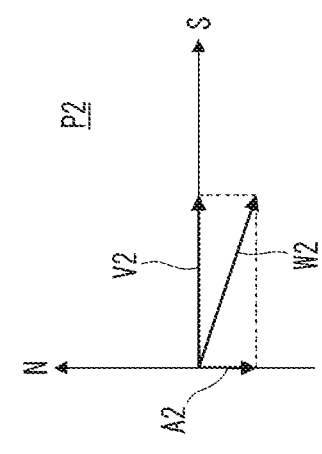
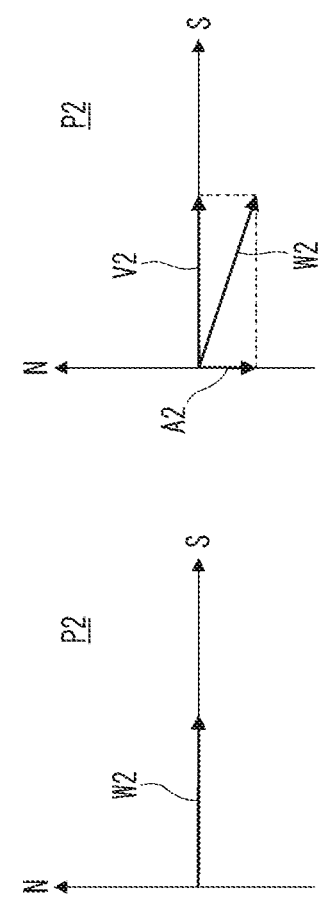
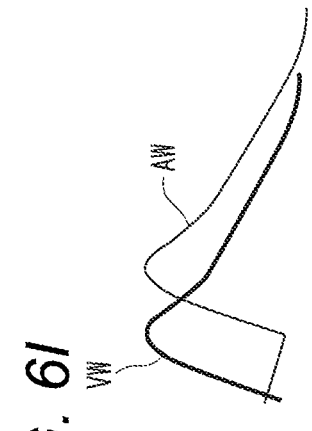
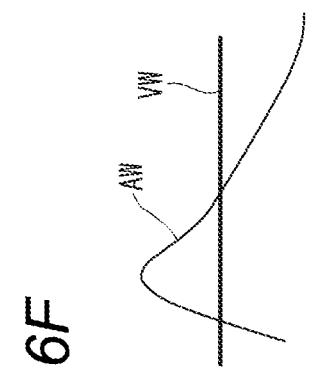
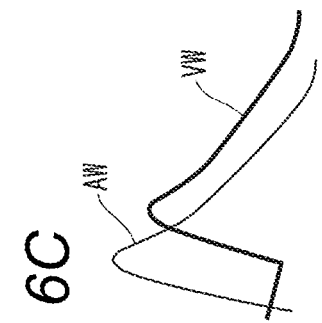

PULSE OXIMETER

CROSS-REFERENCE TO RELATED APPLICATION

The present application claims priority from Japanese Patent Application No. 2017-164265 filed on Aug. 29, 2017, the entire content of which is incorporated herein by reference.

BACKGROUND

The presently disclosed subject matter relates to a pulse oximeter.

A pulse oximeter is an example of a device for calculating transcutaneous arterial oxygen saturation (SpO2) of a subject. Specifically, a tissue of the subject is irradiated with light of a plurality of wavelengths having different ratios of blood extinction coefficients in accordance with the arterial oxygen saturation. For each wavelength, amount of light transmitted through or reflected by the tissue are detected. The amount of light of each wavelength changes in accordance with a pulsation of the arterial blood of the subject. Therefore, temporal variation of the amount of light of each wavelength due to the pulsation are acquired in the form of pulse wave signals. The amplitude of a pulse wave signal of each wavelength corresponds to a light attenuation variation of the wavelength. The arterial oxygen saturation is calculated based on a ratio of the light attenuation variations of the respective wavelengths. For example, such a pulse oximeter is disclosed in JP4196209B2.

Generally, it is said that pulsation does not occur in the venous blood. A tissue of a subject to be irradiated with light, however, has a region where arterial capillary vessels and venous capillary vessels both exist. This region includes blood in which the oxygen saturation is relatively high and also blood in which the oxygen saturation is relatively low. The calculated value of the arterial oxygen saturation in this region is inevitably affected by the venous blood flowing through venous capillary vessels. To improve calculation accuracy of the arterial oxygen saturation, the tissue is sometimes pressed to remove the venous blood and to reduce an influence of the venous blood.

SUMMARY

The presently disclosed subject matter relates to a pulse oximeter with an improved calculation accuracy of arterial oxygen saturation.

According to an aspect of the presently disclosed subject matter, a pulse oximeter includes one or more processor and one or more memory storing instructions executable by the one or more processor. When the instructions are executed by the one or more processor, the one or more processor causes the pulse oximeter to perform operations including acquiring a first signal corresponding to an intensity of first light having a first wavelength, the first light being transmitted through or reflected by a tissue of a subject, acquiring a second signal corresponding to an intensity of second light having a second wavelength, the second light being transmitted through or reflected by the tissue, setting a presumptive value of an arterial oxygen saturation, acquiring, from the first signal and the second signal, an arterial blood component signal and a venous blood component signal corresponding to the presumptive value, acquiring an index value corresponding to a phase difference between the arterial blood component signal and the venous blood component signal, and calculating the arterial oxygen saturation based on a variation of the index value associated with a change of the presumptive value.

Related art pulse oximeters calculate the arterial oxygen saturation, directly from acquired first and second signals (the observed signals). However, as described above the value of a calculated arterial oxygen saturation is inevitably affected by venous blood flowing through capillary vessels in a tissue to which a probe is attached. Namely, the observed signals contain an arterial blood component signal and venous blood component signal which have a phase difference.

In view of this, the inventor has separated an arterial blood component signal and a venous blood component signal from observed signals, and studied in detail relationships between a value of the oxygen saturation and a value of the phase difference. Specifically, a variation of the value of the phase difference has been observed while changing the value of the oxygen saturation. As a result, it has been found that the value of the oxygen saturation at which the value of the phase difference exhibits a distinctive change is well consistent with the oxygen saturation of the arterial blood component.

In the above-described pulse oximeter, the arterial oxygen saturation is not calculated directly from the first and second signals (observed signals) which are acquired from the subject, but the presumptive value of the arterial oxygen saturation is first set. Then, a calculation operation using the presumptive value is applied to the observed signals. Thereafter, the arterial blood component signal and the venous blood component signal are separated, and the index value corresponding to the phase difference between the two signals is acquired. The distinctive change described above can be identified by observing a variation of the phase difference while changing the presumptive value of the arterial oxygen saturation. The presumptive value at which the distinctive change is observed is deemed as the arterial oxygen saturation of the subject.

BRIEF DESCRIPTION OF DRAWINGS

FIGS. 6A to 6I illustrate the process to be performed by the pulse oximeter of FIG. 1;

DETAILED DESCRIPTION

Figure 1:
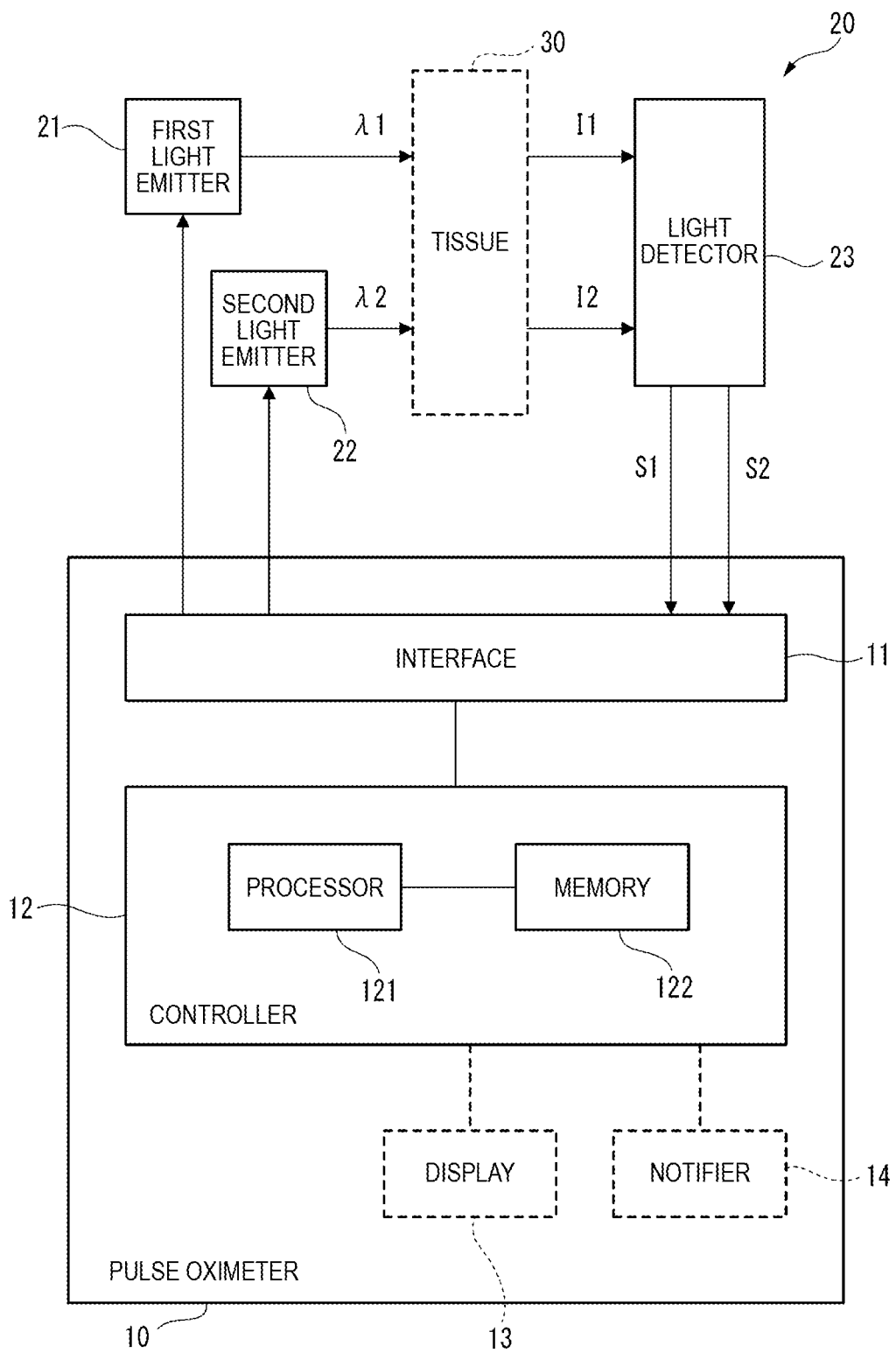
FIG. 1 is a diagram illustrating a functional configuration of a pulse oximeter according to an embodiment of the presently disclosed subject matter.

Hereinafter, embodiments of presently disclosed subject matter will be described in detail with reference to the drawings. FIG. 1 is a diagram illustrating a functional configuration of a pulse oximeter 10 according to an embodiment of the presently disclosed subject matter. The pulse oximeter 10 can include an interface 11 and a controller 12.

The interface 11 is a connector configured to allow transmission of signals. The interface 11 can be connected to a probe 20 in a wired or wireless manner.

The probe 20 is configured to be attached to a tissue 30 (e.g., a fingertip or an earlobe) of a subject. The probe 20 can include a first light emitter 21, a second light emitter 22, and a light detector 23.

The first light emitter 21 is configured to emit first light having a first wavelength $\lambda 1$. For example, the first wavelength $\lambda 1$ may be 880 nm or 940 nm, that is, the first light may be infrared light. The second light emitter 22 is configured to emit second light having a second wavelength $\lambda 2$. For example, the second wavelength $\lambda 2$ may be 630 nm or 660 nm, that is, the second light may be red light.

The first light emitter 21 is, for example, a semiconductor light emitting device configured to emit the first light. The second light emitter 22 is, for example, a semiconductor light emitting device configured to emit the second light. Examples of the semiconductor light emitting devices include light emitting diodes (LEDs), laser diodes, and organic electroluminescence devices.

As illustrated in FIG. 1, the light detector 23 is configured to output a first intensity signal S1 corresponding to the intensity I1 of the first light transmitted through or reflected by a tissue 30 of the subject. The light detector 23 is configured to output a second intensity signal S2 corresponding to the intensity I2 of the second light transmitted through or reflected by the tissue 30.

The light detector 23 is, for example, an optical sensor sensitive to the first wavelength $\lambda 1$ and the second wavelength $\lambda 2$. Examples of the optical sensor include a photodiode, a phototransistor, and a photoresistor.

The controller 12 includes at least one or more processor 121 and at least one or more memory 122. Examples of the processor 121 include a CPU and an MPU. The memory 122 is configured to store instructions which can be executed by the processor 121. Examples of the memory 122 are a ROM which stores various instructions, and a RAM having a work area in which various instructions to be executed by the processor 121 are stored.

Figure 2:
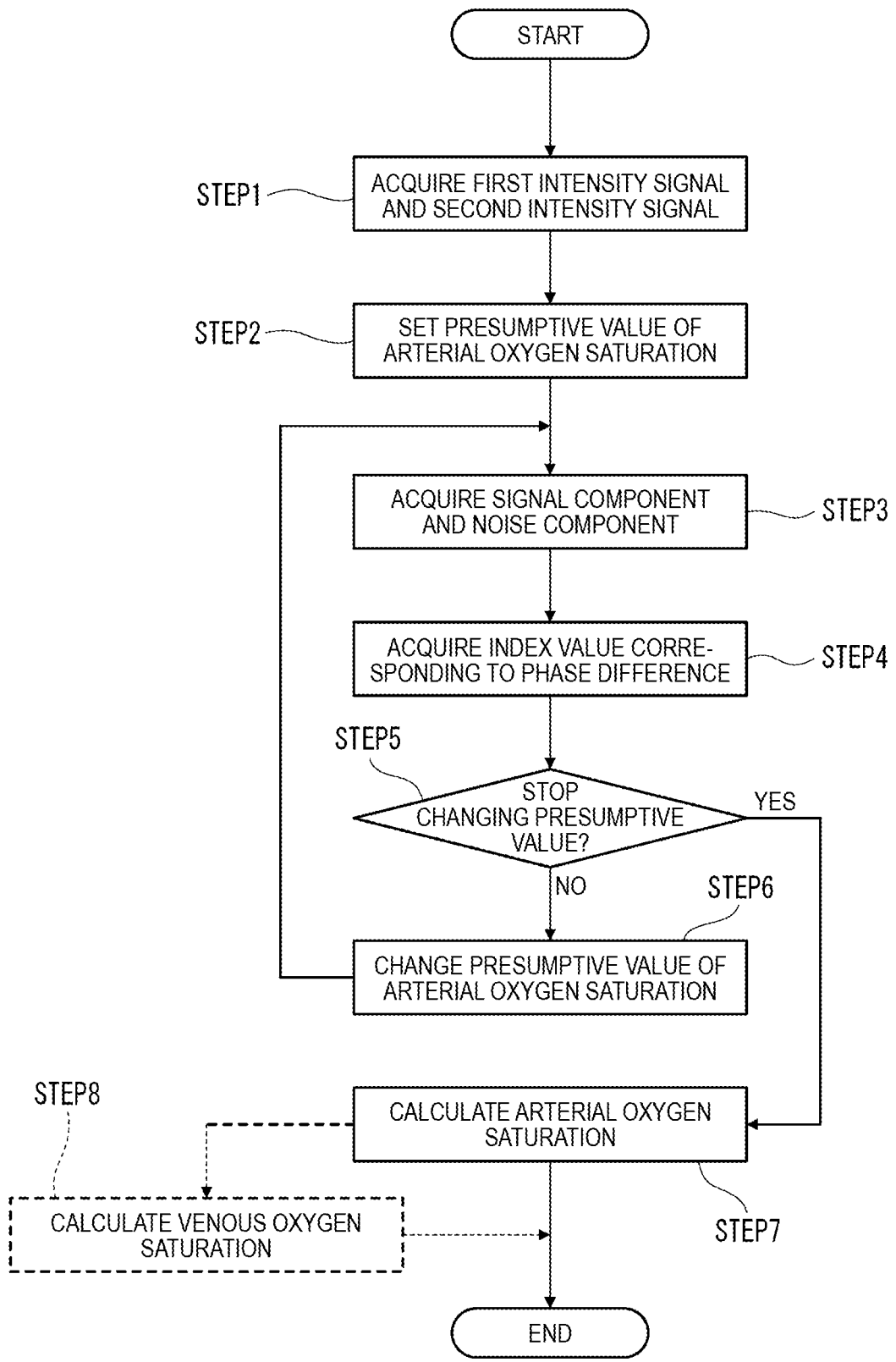
FIG. 2 is a flowchart of a process to be performed by the pulse oximeter of FIG. 1.

The pulse oximeter 10 is configured to, when instructions stored in the memory 122 are executed by the processor 121, execute the process illustrated in FIG. 2.

First, the first intensity signal S1 and the second intensity signal S2 are acquired (STEP 1). Specifically, the first light emitter 21 and the second light emitter 22 are alternately lighted based on a control signal which is output from the controller 12 through the interface 11. Therefore, the first intensity signal S1 and the second intensity signal S2 are alternately output from the light detector 23 with accompanying a time difference. The switching frequency of the light emission timings of the first light emitter 21 and the second light emitter 22 is set to a degree at which the acquisitions of the first and second intensity signals S1, S2 can be deemed substantially simultaneous with each other as compared with temporal variation of the calculated arterial oxygen saturation. The controller 12 acquires the first intensity signal S and the second intensity signal S2 through the interface 11.

In order to perform one set of process for calculating one arterial oxygen saturation, the first intensity signal S1 and the second intensity signal S2 are acquired over a predetermined time period. An example of the predetermined time period is four seconds (a time period equivalent to about three heart beats).

Figure 3A:
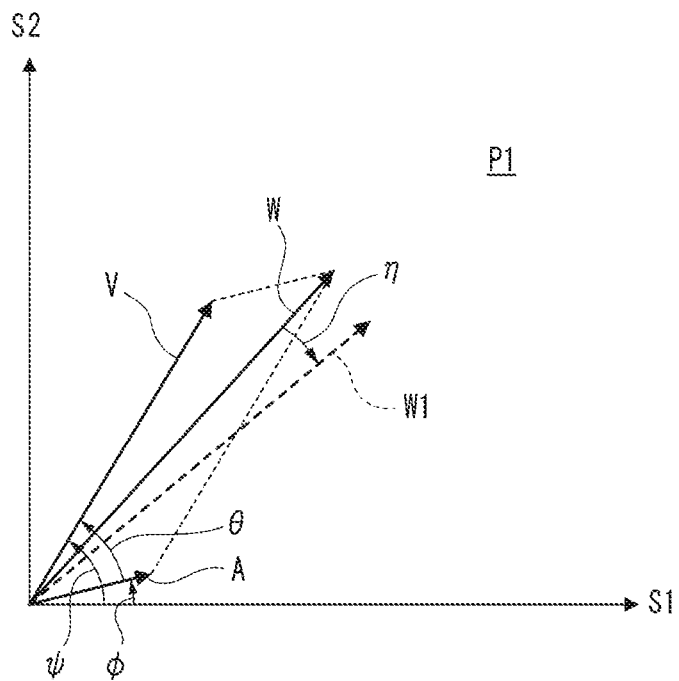
FIGS. 3A and 3B illustrate the process to be performed by the pulse oximeter of FIG. 1.

FIG. 3A illustrates a coordinate plane P1. The abscissa of the coordinate plane P1 indicates the value of the first intensity signal S1. The ordinate of the coordinate plane P1 indicates the value of the second intensity signal S2. A temporal variation of the value of the first intensity signal S1 and a temporal variation of the value of the second intensity signal S2 in the predetermined time period define a linear locus on the coordinate plane P1. The locus can be expressed as an observed signal vector W. The observed signal vector W can be expressed as the resultant vector of an arterial blood component vector A and a venous blood component vector V. This fact will be described with reference to FIG. 4.

Figure 4:
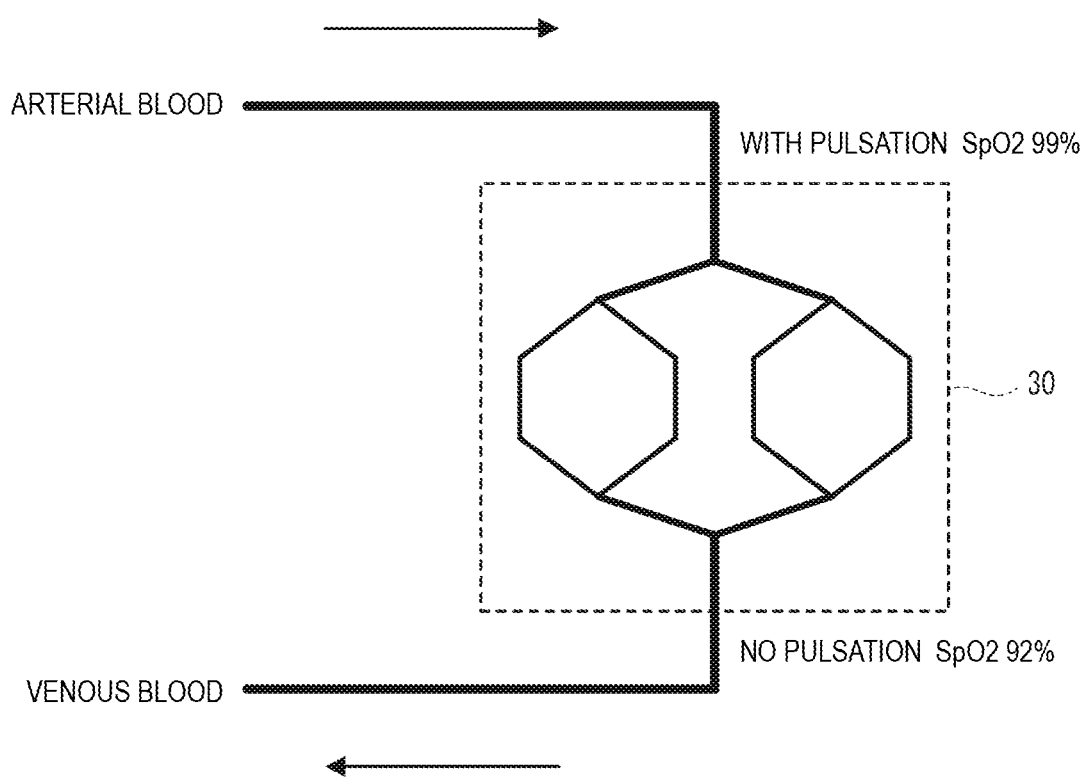
FIG. 4 illustrates the process to be performed by the pulse oximeter of FIG. 1.

The region which is indicated by the broken line in FIG. 4 indicates the tissue 30 of the subject to which the probe 20 is to be attached. The arterial blood which flows into the tissue 30 involves pulsations. It is assumed that the value of the oxygen saturation of the arterial blood is 99%. The venous blood which flows out from the tissue 30 is deemed not to involve pulsations. It is assumed that the value of the oxygen saturation of the venous blood is 92%.

In the above case, the value of the arterial oxygen saturation which is calculated by the pulse oximeter 10 should be 99%. In the tissue 30 to which the probe 20 is to be attached, however, capillary vessels through which the arterial blood flows, and those through which the venous blood flows are mixed, and therefore the value is inevitably affected by the latter in which the oxygen saturation is relatively low. In the case of a conventional pulse oximeter, consequently, the value of calculated arterial oxygen saturation is sometimes lower than that of the actual one (for example, 94%).

In the example illustrated in FIG. 3A, the observed signal vector W corresponds to the arterial oxygen saturation calculated by a related art pulse oximeter. As described above, the observed signal vector W corresponds to a locus on the coordinate plane P1, drawn by the temporal variations of the first and second intensity signals S1, S2. The temporal variations of the first and second intensity signals S1, S2 obtained from the tissue 30 are affected by both the arterial blood in which the oxygen saturation is 99%, and the venous blood in which the oxygen saturation is 92%. The former corresponds to the arterial blood component vector A, and the latter corresponds to the venous blood component vector V. Therefore, the observed signal vector W can be expressed as the resultant vector of the arterial blood component vector A and the venous blood component vector V.

The pulse oximeter 10 is configured to identify the arterial blood component vector A which does not directly appear in the temporal variations of the first and second intensity signals S1, S2, and to calculate an arterial oxygen saturation corresponding to the identified arterial blood component vector A.

The arterial oxygen saturation to be calculated is unknown. Thus, as illustrated in FIG. 2, the pulse oximeter 10 sets a presumptive value PSA of the arterial oxygen saturation (STEP 2), and acquires a signal component and a noise component (STEP 3). For example, an initial presumptive value PS may be 100%.

Figure 3B:
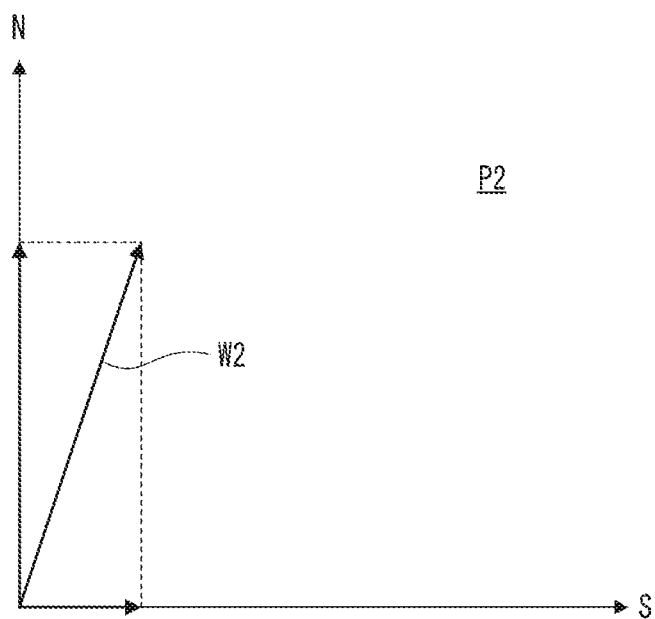

These steps are equivalent to rotating the observed signal vector W clockwise by a rotation angle η about the origin of the coordinate plane P1 to obtain a vector W1 as illustrated in FIG. 3A, and transforming the vector W1 into a vector W2 on a coordinate plane P2 as illustrated in FIG. 3B.

Although not illustrated, the vector W1 is a resultant vector of an arterial blood component vector A1 and venous blood component vector V1 which are rotated by the rotation angle η. The abscissa of the coordinate plane P2 indicates the signal component of pulsations necessary for calculating the arterial oxygen saturation. The ordinate of the coordinate plane P2 indicates a noise component which impedes the calculation of the arterial oxygen saturation.

In FIG. 3A, φ indicates the angle of the arterial blood component vector A with the abscissa of the coordinate plane P1. ψ indicates the angle of the venous blood component vector V with the abscissa of the coordinate plane P1. θ indicates the angle formed by the arterial blood component vector A and the venous blood component vector V. Then, the following expression is obtained:

$$\theta = \psi - \phi$$

It is known that, at this time, the coordinate transformation from the coordinate plane P1 to the coordinate plane P2 is expressed by the following expression:

$$\begin{pmatrix} S \\ N \end{pmatrix} = \begin{pmatrix} 1 & -\frac{1}{\tan\theta} \\ 0 & -\frac{1}{\sin\theta} \end{pmatrix} \begin{pmatrix} \cos\phi & \sin\phi \\ -\sin\phi & \cos\phi \end{pmatrix} \begin{pmatrix} S1 \\ S2 \end{pmatrix}$$

It is known that the arterial oxygen saturation is a function of the extinction ratio Φ of the tissue 30. Namely, the following expression is obtained:

$$PSA = f(\Phi)$$

The extinction ratio Φ is a ratio of light attenuation of the first light and light attenuation of the second light, the first light and the second light being transmitted through or reflected by the tissue 30. It is known that the relationship between the extinction ratio Φ and the angle φ is expressed by the following expression:

$$\phi = \tan^{-1}\Phi$$

When the presumptive value PSA of the arterial oxygen saturation is determined, namely, also the presumptive value of the angle φ of the arterial blood component vector A is determined.

On the other hand, also the angle ψ is unknown. Therefore, the value of θ is changed from (−φ) to (π/2−φ) (the value of ψ is changed from 0 to π/2), and the value θ(ψ) is determined as the value at which the norm in the abscissa direction of the coordinate plane P2 is minimum.

When the values of φ and θ which are determined in this way are substituted into the foregoing coordinate transformation expression, the coordinate transformation illustrated in FIG. 3B is completed. The coordinate transformation corresponds to an operation in which an arterial blood component vector A2 is made coincident with the abscissa indicating a signal component S, and a venous blood component vector V2 is made coincident with the ordinate indicating a noise component N. The vector W2 is the resultant vector of the arterial blood component vector A2 and the venous blood component vector V2.

In this way, the signal component S and the noise component N are separated from the first and second intensity signals S1, S2 acquired through the probe 20. The locus of temporal variation of the signal component S defines the arterial blood component vector A, and the locus of temporal variation of the noise component N defines the venous blood component vector V.

Figure 5A:
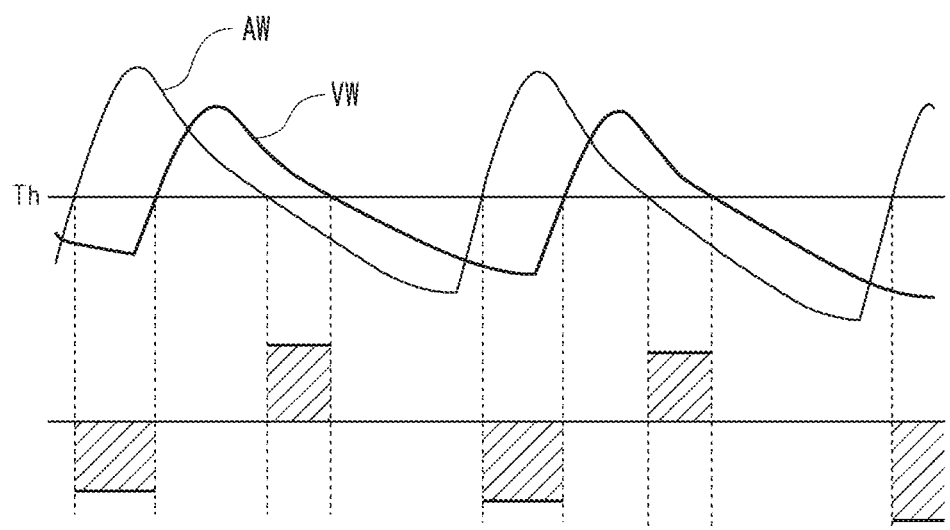
FIGS. 5A and 5B illustrate the process to be performed by the pulse oximeter of FIG. 1.

Consequently, as illustrated in FIG. 5A, an arterial blood component signal AW formed by the temporal variation of the signal component S, and a venous blood component signal VW formed by the temporal variation of the noise component N are obtained.

There is a phase difference between the arterial blood component signal AW and the venous blood component signal VW. The value of the phase difference varies in accordance with the rotation angle η of the observed signal vector W illustrated in FIG. 3A.

FIG. 6A illustrates the vectors W1, A1, V1 obtained by a rotation operation corresponding to a case where the presumptive value PSA of the arterial oxygen saturation is 99%. FIG. 6B illustrates the vectors W2, A2, V2 obtained by the coordinate transformation described above. FIG. 6C illustrates the arterial blood component signal AW and the venous blood component signal VW obtained in this case. There is a phase difference between the two waveforms.

FIG. 6D illustrates the vectors W1, A1, V1 obtained by a rotation operation corresponding to a case where the presumptive value PSA of the arterial oxygen saturation is 94%. In this case, as illustrated in FIG. 6E, the venous blood component is extinguished, and only the arterial blood component vector A2 is obtained as a result of the coordinate transformation. As illustrated in FIG. 6F, therefore, only the arterial blood component signal AW is obtained, and the phase difference cannot be defined.

FIG. 6G illustrates the vectors W1, A1, V1 obtained by a rotation operation corresponding to a case where the presumptive value PSA of the arterial oxygen saturation is 92%. FIG. 6H illustrates the vectors W2, A2, V2 obtained by the coordinate transformation. FIG. 6I illustrates the arterial blood component signal AW and the venous blood component signal VW obtained in this case. Between the two waveforms, there is a phase difference which is different from that in the case of FIG. 6C.

The pulse oximeter 10 is configured to monitor how the phase difference varies, while changing the presumptive value PSA of the arterial oxygen saturation.

As illustrated in FIG. 2, the pulse oximeter 10 acquires an index value IDX corresponding to the phase difference, with respect to the presumptive value PSA (100%) of the arterial oxygen saturation which is initially set (STEP 4).

In the embodiment, as illustrated in FIG. 5A, the index value IDX is acquired based on a time period in which one of the arterial blood component signal AW and the venous blood component signal VW is lower than a threshold Th. More specifically, the value is increased during a time period in which the arterial blood component signal AW is lower than the threshold Th, and decreased during a time period in which the venous blood component signal VW is lower than the threshold Th. The value is increased and decreased over the entire series of the arterial blood component signal AW and the venous blood component signal VW which has been acquired, and the final value is used as the index value IDX.

Next, the pulse oximeter 10 determines whether a condition for stopping the changing of the presumptive value PSA of the arterial oxygen saturation is satisfied (STEP 5 of FIG. 2). If not satisfied (STEP 5; N), the pulse oximeter 10 changes the presumptive value PSA of the arterial oxygen saturation (STEP 6). For example, the presumptive value PSA is changed from 100% to 99%. With the changed presumptive value PSA, STEP 3 and STEP 4 described above are repeated, and the index value IDX corresponding to the new phase difference is obtained.

While changing the presumptive value PSA of the arterial oxygen saturation, the index value IDX corresponding to the presumptive value PSA is repeatedly obtained until the condition for stopping the changing is satisfied (STEP 5, Y). As a result, relationships between the presumptive value PSA and the index value IDX are acquired as exemplified in FIG. 5B, As can be seen from FIG. 5B, when the presumptive value PSA of the arterial oxygen saturation is decreased to the vicinity of 99%, a variation of the index value IDX increases. In a region (the vicinity of 94%) where the presumptive value PSA is further decreased, the index value IDX steeply varies up and down. When the presumptive value PSA is further decreased (the vicinity of 92%), the variation of the index value IDX again becomes small. In other words, when the presumptive value PSA is increased to a certain value (the vicinity of 92%), the variation of the index value IDX increases. When the presumptive value PSA is further increased (the vicinity of 99%) via the region where the index value IDX steeply varies up and down, the variation of the index value IDX again becomes small. With the steeply up and down region being excluded, there are two presumptive values PSA at which the variation of the index value IDX increases.

The pulse oximeter 10 calculates the arterial oxygen saturation SA based on the variation of the index value IDX (STEP 7 of FIG. 2).

Figure 5B:
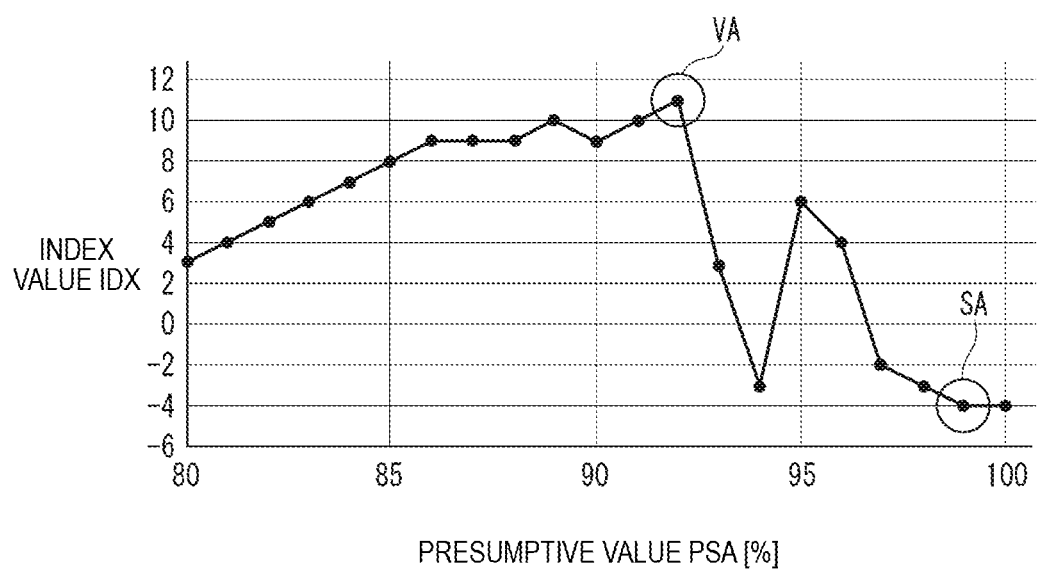

Specifically, the larger one of the two presumptive values PSA at which the variation of the index value IDX increases is deemed as the arterial oxygen saturation SA. In the example of FIG. 5B, the calculated arterial oxygen saturation SA is 99%.

More specifically, the pulse oximeter 10 calculates the quadratic differential value of the index value IDX obtained with a change of the presumptive value PSA of the arterial oxygen saturation. The pulse oximeter 10 determines that the larger one of the two presumptive values PSA at which the quadratic differential value exceeds a threshold is the value of the arterial oxygen saturation SA.

As indicated by broken lines in FIG. 1, the pulse oximeter 10 may include a display 13. In this case, the calculated arterial oxygen saturation SA may be displayed on the display 13.

As indicated by broken lined in FIG. 2, the pulse oximeter 10 may calculate the venous oxygen saturation VA based on the variation of the index value IDX (STEP 8).

Specifically, the smaller one of the two presumptive values PSA at which the variation of the index value IDX increases is deemed as the venous oxygen saturation VA. In the example of FIG. 5B, the calculated venous oxygen saturation VA is 92%. The calculated venous oxygen saturation VA may be displayed on the display 13.

More specifically, the pulse oximeter 10 calculates the quadratic differential value of the index value IDX obtained with a change of the presumptive value PSA of the arterial oxygen saturation. The pulse oximeter 10 determines that the smaller one of the two presumptive values PSA in which the quadratic differential value exceeds the threshold is the value of the venous oxygen saturation VA.

Figure 7A:
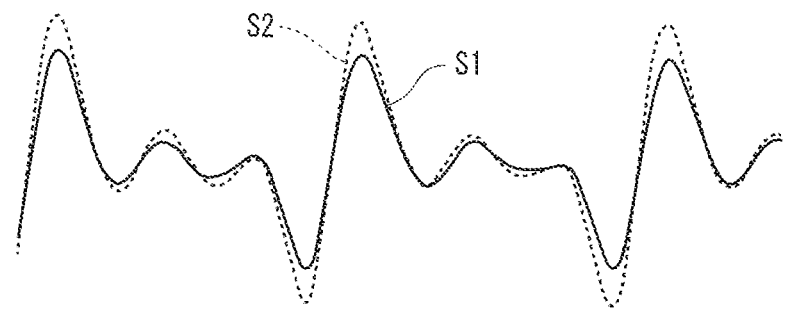
FIGS. 7A to 7C illustrate results of the process to be performed by the pulse oximeter of FIG. 1.
Figure 7B:
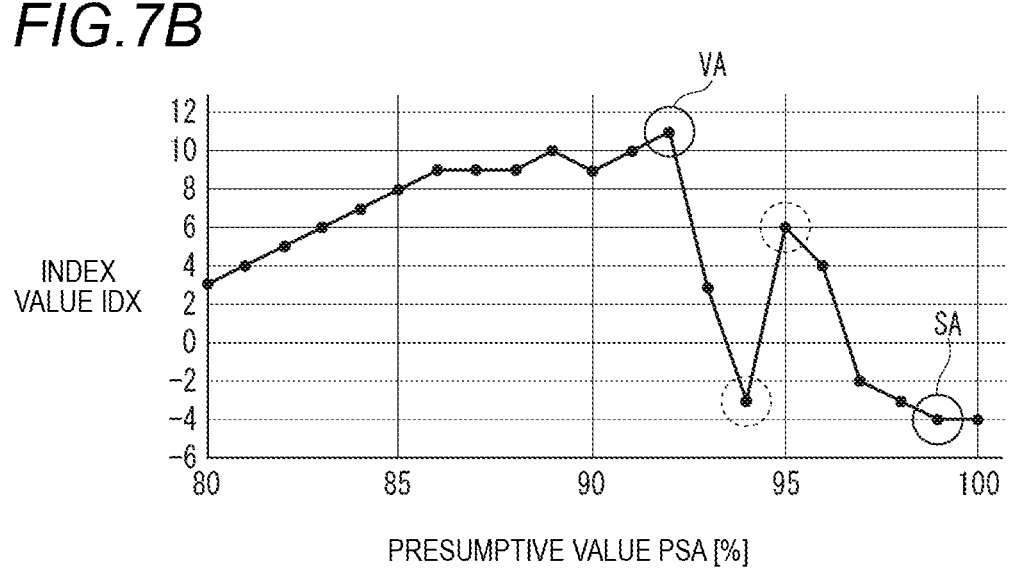
Figure 7C:
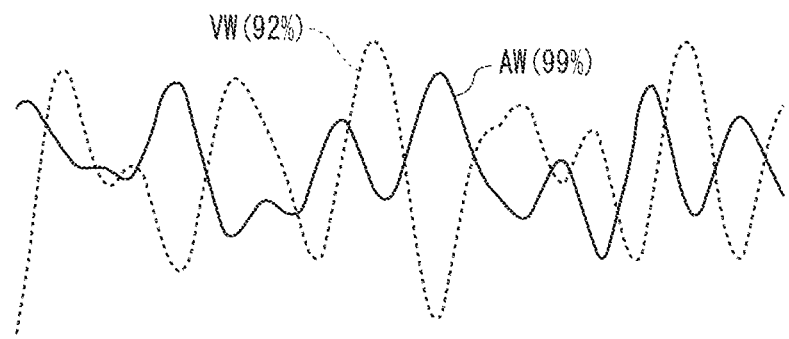

FIGS. 7A to 7C illustrate examples of information that may be displayed on the display 13, among the information obtained in the course of the process described above.

FIG. 7A illustrates a waveform representing a temporal variation of the first intensity signal S1 acquired in STEP 1, and another waveform representing a temporal variation of the second intensity signal S2 acquired in STEP 1.

FIG. 7B illustrates relationships between the index value IDX corresponding to the phase difference between the arterial blood component signal and venous blood component signal which are acquired based on the first and second intensity signals S1, S2 illustrated in FIG. 7A, and the presumptive value PSA of the arterial oxygen saturation. The information illustrated in FIG. 7B is identical with that illustrated in FIG. 5B.

FIG. 7C illustrates the arterial blood component signal AW corresponding to the arterial oxygen saturation SA calculated based on the variation of the index value IDX illustrated in FIG. 7B, and the venous blood component signal VW corresponding to the venous oxygen saturation VA calculated based on the variation of the index value IDX illustrated in FIG. 7B. The arterial blood component signal AW illustrated in FIG. 7C corresponds to a temporal variation of a point defining the arterial blood component vector A2 illustrated in FIG. 6B. The venous blood component signal VW illustrated in FIG. 7C corresponds to a temporal variation of a point defining the venous blood component vector V2 illustrated in FIG. 6H.

The variation of the index value IDX illustrated in FIG. 7B exhibits a steep up and down in a region where the presumptive value PSA of the arterial oxygen saturation is about 94%. The region corresponds to a case illustrated in FIGS. 6D to 6F, and in which the phase difference between the arterial blood component signal and the venous blood component signal cannot be defined. At least in the calculation of the arterial oxygen saturation SA, the pulse oximeter 10 ignores large variations of the index value IDX indicated by the broken line circles in the region.

Figure 8A:
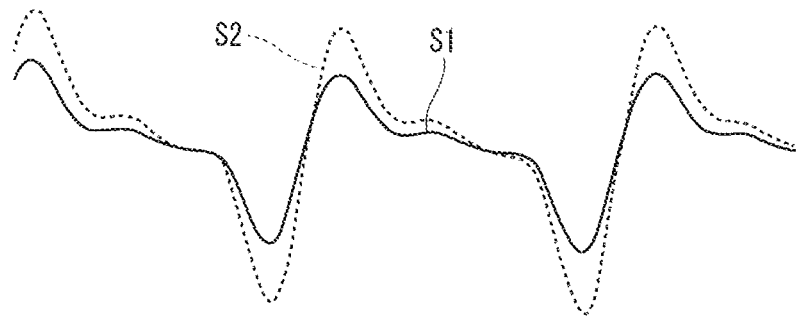
FIGS. 8A to 8C illustrate results of the process to be performed by the pulse oximeter of FIG. 1.
Figure 8B:
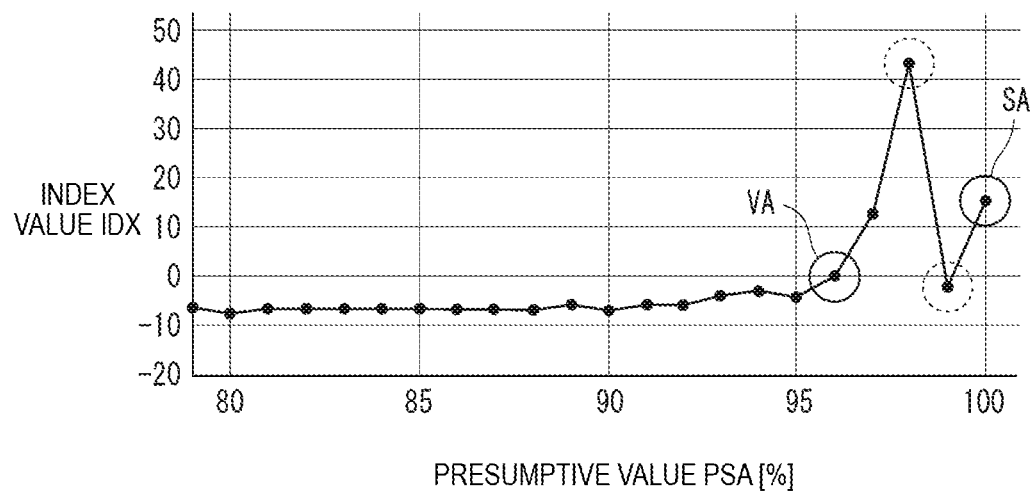
Figure 8C:
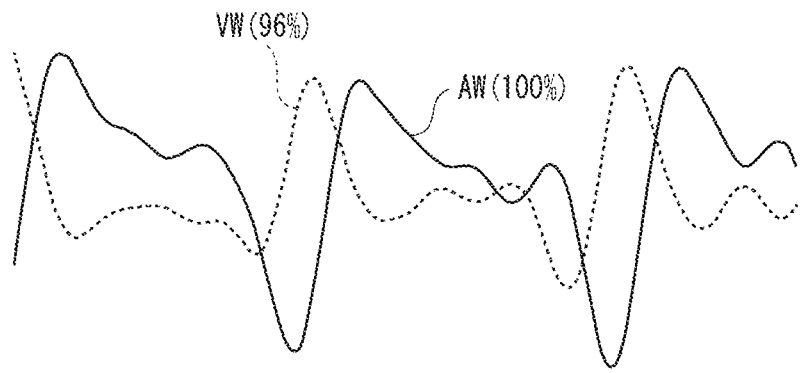

FIGS. 8A to 8C illustrate other examples of information obtained in the course of the process described above. These examples illustrate a case where the influence due to venous pulsation is relatively small as compared with the examples illustrated in FIGS. 7A to 7C. In this case, the calculated arterial and venous oxygen saturations SA, VA are 100% and 96%, respectively.

According to the pulse oximeter 10 described above, an influence of venous blood flowing though capillary vessels in the tissue 30 of the subject can be computationally eliminated without a special structural change to the probe 20 to be attached to the tissue 30. Therefore, the calculation accuracy of the arterial oxygen saturation SA obtained by the pulse oximeter 10 can be improved, without need for pressing the tissue 30 to remove venous blood.

As in the embodiment described above, the arterial oxygen saturation SA may be calculated based on the quadratic differential value of the index value IDX obtained with the presumptive value PSA of the arterial oxygen saturation being changed.

With this configuration, the arterial oxygen saturation SA can be calculated by a simple computation, i.e., acquiring of the quadratic differential value of the index value IDX. Therefore, the processing load of the processor 121 can be prevented from being increased.

As in the embodiment described above, the index value IDX may be acquired based on the time period during which one of the arterial blood component signal AW and the venous blood component signal VW is below the threshold Th.

With this configuration, the index value IDX can be calculated by a relatively simple computation. Therefore, the processing load of the processor 121 can be prevented from being increased.

The index value IDX may be acquired based on a time period during which one of the arterial blood component signal AW and the venous blood component signal VW is above the threshold Th. The index value IDX may be acquired also by the fast Fourier transform, the Fourier transform, the maximum entropy method, the adaptive filtering method, or the like.

According to the pulse oximeter 10 described above, the venous oxygen saturation of the subject can also be calculated without a special structural change to the probe 20 to be attached to the tissue 30 of the subject, without need for pressing the tissue 30 to remove venous blood.

The phase difference between the arterial blood component signal AW and the venous blood component signal VW can be considered as being caused by the time required for the blood pass through the tissue 30 (see FIG. 4). The time required for the blood of the subject to pass through the tissue 30 may be calculated based on information of the phase difference obtained in the course of the process of calculating the arterial oxygen saturation SA. The calculated time may be displayed on the display 13.

For example, multiple time data corresponding to the phase difference can be acquired from the arterial blood component signal AW and the venous blood component signal VW illustrated in FIG. 5A. The pulse oximeter 10 may then deem the average time as the time required for the blood of the subject to pass through the tissue 30.

With this configuration, the time required for the blood of the subject to pass through the tissue 30 of the subject can be calculated without a special structural change to the probe 20 to be attached to the tissue 30.

As indicated by broken lines in FIG. 1, the pulse oximeter 10 may include a notifier 14. The notifier 14 may be configured to perform a notification when the calculated arterial oxygen saturation SA is below a predetermined value. The notification may include at least one of a visual notification, an audible notification, and a haptic notification.

With this configuration, a highly accurate notification may be provided to the user based on the arterial oxygen saturation SP calculated with improved accuracy.

While the presently disclosed subject matter has been described with reference to a certain embodiment thereof, it will be understood by a person skilled in the art that various changes and modifications can be made therein.

In the embodiment described above, at least one of the first intensity signal S1, the second intensity signal S2, the relationships between the presumptive value PSA of the arterial oxygen saturation and the index value IDX, the arterial blood component signal AW, the venous blood component signal VW, the arterial oxygen saturation SA, the venous oxygen saturation VA, and the time period when the blood of the subject is passed through the tissue 30 may be displayed on the display 13 of the pulse oximeter 10. However, such information may be displayed on a separate display device connected to the pulse oximeter 10 in a wired or wireless manner.

The arterial oxygen saturation is an example of blood light absorber concentration. The presently disclosed subject matter is applicable also to a device configured to calculate another kind of blood light absorber concentration (i.e., a pulse photometer). Examples of the other blood light absorber concentration include carboxyhemoglobin, methemoglobin, and a pigment injected into the blood. In this case, the wavelengths of light used in the probe 20 are selected such that a ratio of a blood extinction coefficient with one of the wavelengths, and a blood extinction coefficient with the other wavelength varies in accordance with the concentration of the target light absorber contained in the blood.

According to this embodiment of the presently disclosed subject matter, the pulse photometer includes one or more processor and one or more memory storing instructions executable by the one or more processor. When the instructions are executed by the one or more processor, the one or more processor causes the pulse photometer to perform operations including acquiring a first signal corresponding to an intensity of first light having a first wavelength, the first light being transmitted through or reflected by a tissue of a subject, acquiring a second signal corresponding to an intensity of second light having a second wavelength, the second light being transmitted through or reflected by the tissue, setting a presumptive value of a blood light absorber concentration, acquiring, from the first signal and the second signal, an arterial blood component signal and a venous blood component signal corresponding to the presumptive value, acquiring an index value corresponding to a phase difference between the arterial blood component signal and the venous blood component signal, and calculating the blood light absorber concentration based on a variation of the index value associated with a change of the presumptive value.

The presently disclosed subject matter is also applicable to a device configured to calculate a value of a physiological parameter of a subject based on two signals acquired from the body of the subject and having a phase difference. Examples of such two signals include electrocardiogram signals, electroencephalogram signals, and myoelectric signals.

According to this embodiment of the presently disclosed subject matter, the device includes one or more processor and one or more memory storing instructions executable by the one or more processor. When the instructions are executed by the one or more processor, the one or more processor causes the device to perform operations including acquiring a first vital sign signal from the subject, acquiring a second vital sign signal from the subject, acquiring an index value corresponding to a phase difference between the first vital sign signal and the second vital sign signal, setting a presumptive value of the physiological parameter, and calculating the value of the physiological parameter based on a variation of the index value associated with a change of the presumptive value.

What is claimed is:

1. A pulse oximeter comprising:
   one or more processor; and
   one or more memory storing instructions executable by the one or more processor,
   wherein, when the instructions are executed by the one or more processor, the one or more processor causes the pulse oximeter to perform operations comprising:
   acquiring a first signal corresponding to an intensity of first light having a first wavelength, the first light being transmitted through or reflected by a tissue of a subject,
   acquiring a second signal corresponding to an intensity of second light having a second wavelength, the second light being transmitted through or reflected by the tissue,
   setting a first presumptive value of an arterial oxygen saturation,
   acquiring from the first signal, the second signal, and the first presumptive value, a first arterial blood component signal and a first venous blood component signal corresponding to the first presumptive value,
   acquiring a first index value corresponding to a phase difference between the first arterial blood component signal and the first venous blood component signal,
   setting a second presumptive value of the arterial oxygen saturation, acquiring from the first signal, the second signal, and the second presumptive value, a second arterial blood component signal and a second venous blood component signal corresponding to the second presumptive value, acquiring a second index value corresponding to a phase difference between the second arterial blood component signal and the second venous blood component signal, and calculating a calculated arterial oxygen saturation based on a variation of the first index value and the second index value associated with a change of the first presumptive value to the second presumptive value.

2. The pulse oximeter according to claim 1, wherein the calculated arterial oxygen saturation is calculated based on quadratic differential values of the first index value and the second index value with the first presumptive value and the second presumptive value being changed.

3. The pulse oximeter according to claim 1, wherein the first index value is acquired based on a time period during which one of the first arterial blood component signal and the first venous blood component signal is above or below a threshold, and the second index value is acquired based on a time period during which one of the second arterial blood component signal and the second venous blood component signal is above or below the threshold.

4. The pulse oximeter according to claim 1, wherein, when the instructions are executed by the one or more processor, the one or more processor causes the pulse oximeter to calculate a calculated venous oxygen saturation of the subject based on the variation of the first index value and the second index value associated with the change of the first presumptive value to the second presumptive value.

5. The pulse oximeter according to claim 1, wherein, when the instructions are executed by the one or more processor, the one or more processor causes the pulse oximeter to calculate a time required for blood of the subject to pass through the tissue, based on the phase difference corresponding to the calculated arterial oxygen saturation.

6. The pulse oximeter according to claim 1, wherein the pulse oximeter further includes a notifier configured to perform a notification when the calculated arterial oxygen saturation is below a predetermined value.

7. A pulse photometer comprising:
one or more processor; and
one or more memory storing instructions executable by the one or more processor,
wherein, when the instructions are executed by the one or more processor, the one or more processor causes the pulse photometer to perform operations comprising:
acquiring a first signal corresponding to an intensity of first light having a first wavelength, the first light being transmitted through or reflected by a tissue of a subject,
acquiring a second signal corresponding to an intensity of second light having a second wavelength, the second light being transmitted through or reflected by the tissue, setting a first presumptive value of a blood light absorber concentration, acquiring from the first signal, the second signal, and the first presumptive value, a first arterial blood component signal and a first venous blood component signal corresponding to the first presumptive value, acquiring a first index value corresponding to a phase difference between the first arterial blood component signal and the first venous blood component signal, setting a second presumptive value of the blood light absorber concentration, acquiring from the first signal, the second signal, and the second presumptive value, a second arterial blood component signal and a second venous blood component signal corresponding to the second presumptive value, acquiring a second index value corresponding to a phase difference between the second arterial blood component signal and the second venous blood component signal, and calculating a calculated blood light absorber concentration based on a variation of the first index value and the second index value associated with a change of the first presumptive value to the second presumptive value.

8. A method comprising:
acquiring a first signal corresponding to an intensity of first light having a first wavelength, the first light being transmitted through or reflected by a tissue of a subject,
acquiring a second signal corresponding to an intensity of second light having a second wavelength, the second light being transmitted through or reflected by the tissue,
setting a first presumptive value of a blood light absorber concentration,
acquiring from the first signal and the second signal and the first presumptive value, a first arterial blood component signal and a first venous blood component signal corresponding to the first presumptive value,
acquiring an index value corresponding to a phase difference between the first arterial blood component signal and the first venous blood component signal,
setting a second presumptive value of the blood light absorber concentration,
acquiring from the first signal, the second signal, and the second presumptive value, a second arterial blood component signal and a second venous blood component signal corresponding to the second presumptive value,
acquiring a second index value corresponding to a phase difference between the second arterial blood component signal and the second venous blood component signal, and
calculating a calculated blood light absorber concentration based on a variation of the first index value and the second index value associated with a change of the first presumptive value to the second presumptive value.

* * * * *